(12) United States Patent
Sabelle et al.

(10) Patent No.: US 7,435,267 B2
(45) Date of Patent: Oct. 14, 2008

(54) SECONDARY PARA-PHENYLENEDIAMINES BEARING AN ALKOXY GROUP, DYE COMPOSITION COMPRISING THEM, PROCESSES THEREFOR AND USES THEREOF

(75) Inventors: Stéphane Sabelle, Paris (FR); Jean-Jacques Vandenbossche, Begaar (FR)

(73) Assignee: L'Oreal S.A., Paris (FR)

( * ) Notice: Subject to any disclaimer, the term of this patent is extended or adjusted under 35 U.S.C. 154(b) by 215 days.

(21) Appl. No.: 11/066,449

(22) Filed: Feb. 28, 2005

(65) Prior Publication Data

US 2006/0021158 A1  Feb. 2, 2006

Related U.S. Application Data

(60) Provisional application No. 60/568,666, filed on May 7, 2004.

(30) Foreign Application Priority Data

Feb. 27, 2004  (FR)  .................................. 04 02015

(51) Int. Cl.
 *A61K 7/13* (2006.01)
(52) U.S. Cl. ........................ 8/405; 8/406; 8/408; 8/411; 8/414; 8/415; 564/382
(58) Field of Classification Search ................ 8/405, 8/406, 408, 410, 411, 414, 415, 421; 564/382
See application file for complete search history.

(56) References Cited

U.S. PATENT DOCUMENTS

| | | | |
|---|---|---|---|
| 3,819,708 A | | 6/1974 | Manning et al. |
| RE30,199 E | | 1/1980 | Rose et al. |
| 4,277,244 A | * | 7/1981 | Bugaut et al. .................. 8/410 |
| 4,823,985 A | | 4/1989 | Grollier et al. |
| 5,061,289 A | | 10/1991 | Clausen et al. |
| 5,380,340 A | | 1/1995 | Neunhoeffer et al. |
| 5,534,267 A | | 7/1996 | Neunhoeffer et al. |
| 5,663,366 A | | 9/1997 | Neunhoeffer et al. |
| 5,708,151 A | | 1/1998 | Mockli |
| 5,733,343 A | | 3/1998 | Mockli |
| 5,766,576 A | | 6/1998 | Lowe et al. |
| 6,099,592 A | | 8/2000 | Vidal et al. |
| 6,284,003 B1 | | 9/2001 | Rose et al. |
| 6,730,789 B1 | | 5/2004 | Birault et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 081 790 | 6/1983 |
| EP | 0 714 954 | 6/1996 |
| EP | 0 770 375 | 5/1997 |
| FR | 2 126 314 | 10/1972 |
| FR | 2 362 112 | 3/1978 |
| FR | 2 421 872 | 11/1979 |
| FR | 2 586 913 | 3/1987 |
| FR | 2 733 749 | 11/1996 |
| FR | 2 801 308 | 5/2001 |
| GB | 1 026 978 | 4/1966 |
| GB | 1 048 790 | 11/1966 |
| GB | 1 153 196 | 5/1969 |
| GB | 2 018 302 | 10/1979 |
| GB | 2 018 808 | 10/1979 |
| JP | 63-169571 | 1/1990 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |

OTHER PUBLICATIONS

STIC Search Report dated Feb. 6, 2007.*
Foreign Patent Office Preliminary Search Report for priority application FR 04/02015, dated Oct. 14, 2004.
Synth. Commun. 1990 20 (22), pp. 3537-3545.
Synthesis, vol. 12, 1990, pp. 1147-1148.
Selva, M. et al. "Reaction of Primary Aromatic Amines with Alkyl Carbonates over NaY Faujasite: A Convenient and Selective Access to Mono-N-Alkyl Anilines" Journal of Organic Chemistry, vol. 66, No. 3, 2001, pp. 677-680.
Derwent Abstract to EP 081 790 (1983).
Derwent Abstract to EP 770 375 (1997).
Derwent Abstract to JP 63-169571 (JP 02-019576) (1990).
Chemical Abstracts XP002300693 (accession No. 2004:3592289; RN 346642-23-7).
Chemical Abstracts XP002300694 (accession No. 1962:32336; "The action of urea-formaldehyde resins, as used in the creaseproofing of textiles, on Azo dyes containing amino groups."

* cited by examiner

*Primary Examiner*—Eisa Elhilo
(74) *Attorney, Agent, or Firm*—Finnegan, Henderson, Farabow, Garrett, & Dunner, L.L.P.

(57) ABSTRACT

The present invention relates to novel secondary para-phenylenediamines bearing an alkoxy group, to a process for preparing them, and to their use in the oxidation dyeing of hair. The invention also relates to a composition for dyeing keratin fibers, in particular human keratin fibers such as hair, containing, in a medium that is suitable for dyeing, at least one secondary para-phenylenediamine. Further, the invention relates to a process for dyeing keratin fibers using the aforementioned composition, and to a dyeing kit containing the composition.

22 Claims, No Drawings

SECONDARY PARA-PHENYLENEDIAMINES BEARING AN ALKOXY GROUP, DYE COMPOSITION COMPRISING THEM, PROCESSES THEREFOR AND USES THEREOF

CROSS-REFERENCE TO RELATED APPLICATIONS

This application claims benefit of U.S. Provisional Application No. 60/568,666, filed May 7, 2004, and French Application No. 04/02015, filed Feb. 27, 2004, both of which are herein incorporated by reference.

FIELD OF THE INVENTION

The present disclosure relates to a novel family of secondary para-phenylenediamines bearing an alkoxy group, to their preparation and to their use in the oxidation dyeing of hair.

BACKGROUND OF THE INVENTION

It is known practice to dye keratin fibers, and in particular human hair, with dye compositions containing oxidation dye precursors, such as ortho- or para-phenylenediamines, ortho- or para-aminophenols, and heterocyclic compounds, which are generally referred to as oxidation bases. These oxidation bases are colorless or weakly colored compounds which, when combined with oxidizing products, may give rise to colored compounds by a process of oxidative condensation.

It is also known that the shades obtained with these oxidation bases may be varied by combining them with couplers or coloration modifiers, the latter being chosen, for example, from aromatic meta-diaminobenzenes, meta-aminophenols, meta-diphenols and certain heterocyclic compounds such as indole compounds.

The variety of molecules used as oxidation bases and couplers makes it possible to obtain a wide range of colors.

The "permanent" coloration obtained by means of these oxidation dyes should, moreover, satisfy a number of requirements. The dyes should have no toxicological drawbacks, should allow shades of the desired intensity to be obtained, and/or should have good resistance to external agents such as light, bad weather, washing, permanent waving, perspiration and rubbing.

The dyes should also allow white hairs to be covered and, ideally, be as unselective as possible, i.e., allow the smallest possible differences in coloration to be produced over the entire length of the same keratin fiber, which is generally differently sensitized (i.e., damaged) between its end and its root.

SUMMARY OF THE INVENTION

The present inventor has discovered that it is possible to obtain a novel family of secondary para-phenylenediamines bearing an alkoxy group, capable of giving strong, aesthetic, and sparingly-selective colorations in varied shades, and which show good resistance to the various attacking factors to which the fibers may be subjected. The present disclosure relates to these novel secondary paraphenylenediamines, to a process for their preparation, and to their use in the oxidation dyeing of hair.

Another aspect of the present disclosure relates to compositions for dyeing keratin fibers, in particular human keratin fibers such as hair, comprising at least one secondary para-phenylenediamine bearing an alkoxy group which makes it possible to obtain dyes having the abovementioned advantages. In addition, these compositions have a good toxicological profile.

The present disclosure also relates to a dyeing process using this composition for the dyeing of keratin fibers, in particular human keratin fibers such as hair, and a multi-compartment device or dyeing "kit".

The composition disclosed herein makes it possible in particular to obtain very powerful, sparingly selective and fast, in particular light-fast, dyeing of keratin fibers, while at the same time avoiding the degradation of these fibers.

The above recited advantages of the present disclosure are non-limiting. Other aspects, subjects and advantages of the present disclosure will emerge even more clearly upon reading the description and the non-limiting examples that follow.

DETAILED DESCRIPTION OF THE INVENTION

The novel secondary para-phenylenediamines according to the present disclosure are chosen from compounds of formula (I) and the addition salts thereof:

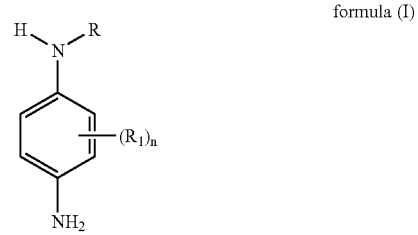

formula (I)

in which:

R is chosen from a linear (linear $(C_1\text{-}C_{10})$alkoxy)$(C_4\text{-}C_{10})$ alkyl radical; a branched (linear $(C_1\text{-}C_{10})$alkoxy)$(C_3\text{-}C_{10})$ alkyl radical; a (branched $(C_3\text{-}C_{10})$alkoxy)$(C_2\text{-}C_{10})$alkyl radical; and a linear or branched $((C_1\text{-}C_{10})$alkoxy)$(C_2\text{-}C_{10})$ alkyl radical substituted with at least one group chosen from hydroxyl, $C_1\text{-}C_{15}$ alkoxy, amino, mono$(C_1\text{-}C_{15})$alkylamino, di$(C_1\text{-}C_{15})$alkylamino, $(C_1\text{-}C_{15})$alkylcarbonyl, amido, $(C_1\text{-}C_{15})$alkoxycarbonyl, mono$(C_1\text{-}C_{15})$alkylaminocarbonyl and di$(C_1\text{-}C_{15})$alkylaminocarbonyl groups.

$R_1$ is chosen from a hydrogen atom, a $C_1\text{-}C_{15}$ alkyl radical, a $C_1\text{-}C_{15}$ alkoxy radical, a $((C_1\text{-}C_{15})$alkoxy)$C_1\text{-}C_{15}$alkyl radical, a $C_1\text{-}C_{15}$ hydroxyalkoxy radical, a $C_1\text{-}C_{15}$ monohydroxyalkyl radical, a $C_1\text{-}C_{15}$ polyhydroxyalkyl radical, and a halogen atom;

n is an integer ranging from 1 to 4;

with the exception of the following compounds:
N-(3-isopropoxypropyl)benzene-1,4-diamine; and
N-(1-methylpropoxypropyl)benzene-1,4-diamine.

In one non-limiting embodiment, the group R in formula (I) is chosen from a linear (linear $(C_1\text{-}C_5)$alkoxy)$(C_4\text{-}C_8)$ alkyl radical; a branched (linear $(C_1\text{-}C_5)$alkoxy)$(C_3\text{-}C_7)$alkyl radical; a (branched $(C_3\text{-}C_7)$alkoxy)$(C_2\text{-}C_6)$alkyl radical; and a linear or branched $((C_1\text{-}C_6)$alkoxy)$(C_2\text{-}C_6)$alkyl radical substituted with at least one group chosen from hydroxyl, $C_1\text{-}C_5$ alkoxy, amino, mono$(C_1\text{-}C_5)$alkylamino, $(C_1\text{-}C_5)$alkylcarbonyl, amido, $(C_1\text{-}C_5)$alkoxycarbonyl, mono$(C_1\text{-}C_5)$alkylaminocarbonyl and di$(C_1\text{-}C_5)$alkylaminocarbonyl groups; and the group $R_1$ of formula (I) is chosen from a hydrogen atom, a $C_1\text{-}C_5$ alkyl radical, a $C_1\text{-}C_5$ alkoxy radical, a $((C_1\text{-}C_5)$alkoxy)$(C_1\text{-}C_5)$alkyl radical, a $C_1\text{-}C_5$ hydroxyalkoxy radical, a $C_1\text{-}C_5$ monohydroxyalkyl radical, a $C_1\text{-}C_5$ polyhydroxyalkyl radical, a chlorine atom and a bromine atom.

The compounds of formula (I) may be chosen from but are not limited to:

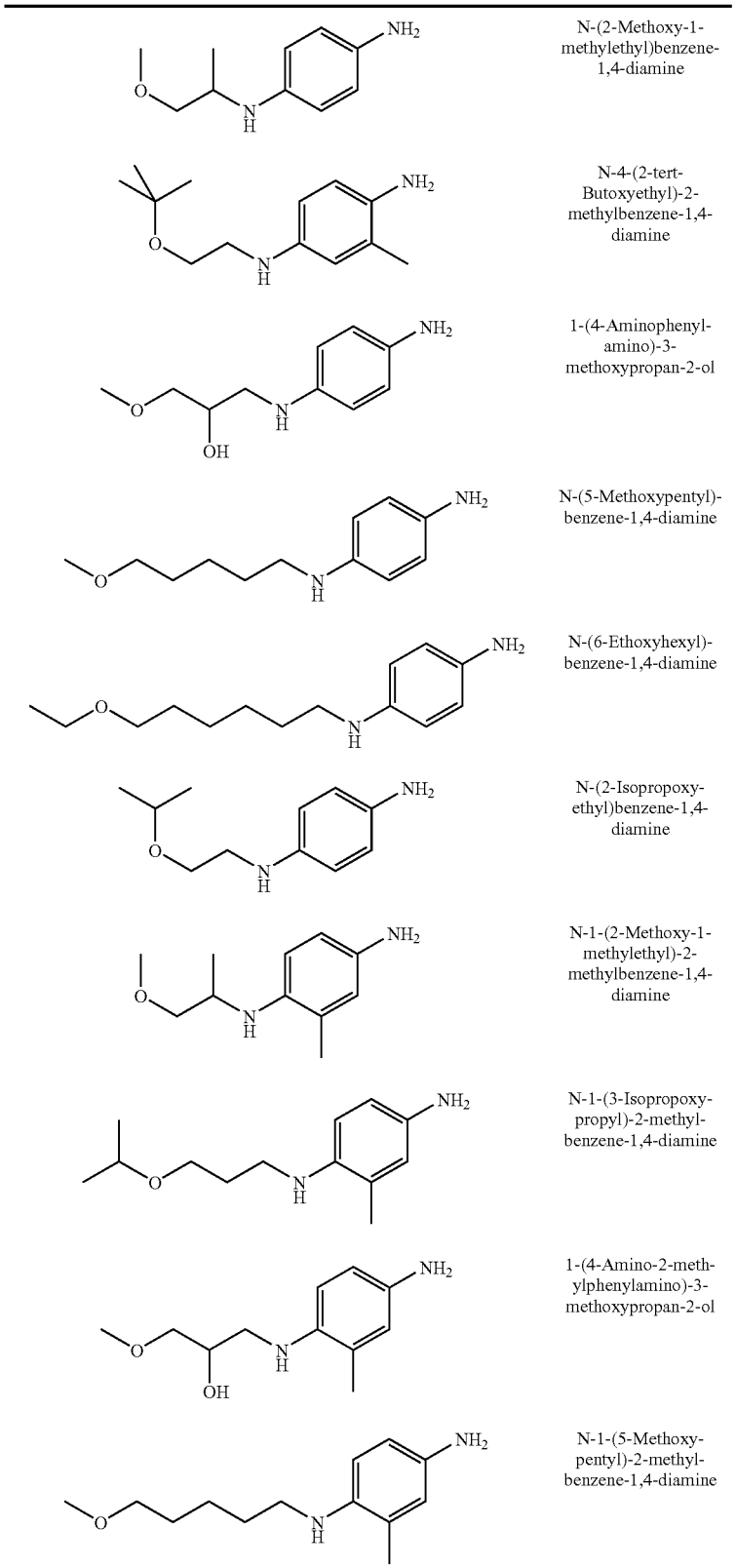

| | |
|---|---|
| | N-(2-Methoxy-1-methylethyl)benzene-1,4-diamine |
| | N-4-(2-tert-Butoxyethyl)-2-methylbenzene-1,4-diamine |
| | 1-(4-Aminophenyl-amino)-3-methoxypropan-2-ol |
| | N-(5-Methoxypentyl)-benzene-1,4-diamine |
| | N-(6-Ethoxyhexyl)-benzene-1,4-diamine |
| | N-(2-Isopropoxy-ethyl)benzene-1,4-diamine |
| | N-1-(2-Methoxy-1-methylethyl)-2-methylbenzene-1,4-diamine |
| | N-1-(3-Isopropoxy-propyl)-2-methyl-benzene-1,4-diamine |
| | 1-(4-Amino-2-methylphenylamino)-3-methoxypropan-2-ol |
| | N-1-(5-Methoxy-pentyl)-2-methyl-benzene-1,4-diamine |

-continued

| Structure | Name |
|---|---|
| | N-1-(6-Ethoxyhexyl)-2-methylbenzene-1,4-diamine |
| | N-1-(2-Isopropoxyethyl)-2-methyl-benzene-1,4-diamine |
| | N-4-(2-Methoxy-1-methylethyl)-2-methylbenzene-1,4-diamine |
| | N-4-(3-Isopropoxypropyl)-2-methyl-benzene-1,4-diamine |
| | 1-(4-Amino-3-methylphenylamino)-3-methoxypropan-2-ol |
| | N-4-(5-Methoxypentyl)-2-methyl-benzene-1,4-diamine |
| | N-4-(6-Ethoxyhexyl)-2-methylbenzene-1,4-diamine |
| | N-4-(2-Isopropoxyethyl)-2-methyl-benzene-1,4-diamine |
| | N-(1-Methoxymethylpropyl)-benzene-1,4-diamine |
| | N-[3-(2-Ethylhexyloxy)propyl]benzene-1,4-diamine |
| | N-(4-Methoxybutyl)benzene-1,4-diamine |

-continued

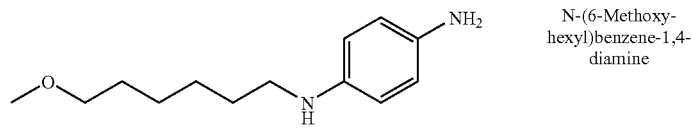 N-(6-Methoxy-hexyl)benzene-1,4-diamine

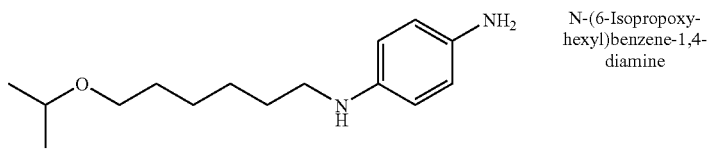 N-(6-Isopropoxy-hexyl)benzene-1,4-diamine

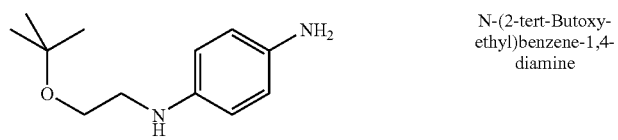 N-(2-tert-Butoxy-ethyl)benzene-1,4-diamine

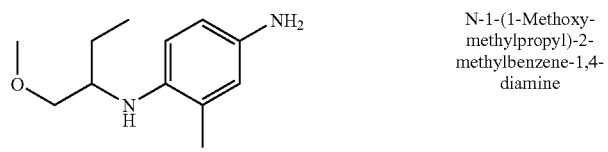 N-1-(1-Methoxy-methylpropyl)-2-methylbenzene-1,4-diamine

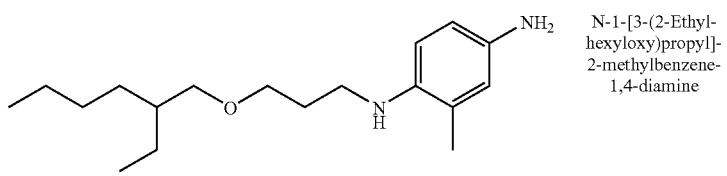 N-1-[3-(2-Ethyl-hexyloxy)propyl]-2-methylbenzene-1,4-diamine

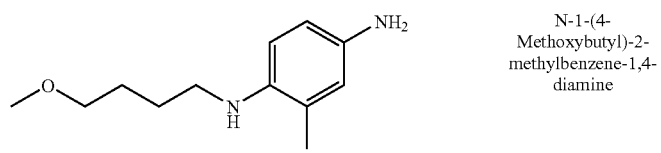 N-1-(4-Methoxybutyl)-2-methylbenzene-1,4-diamine

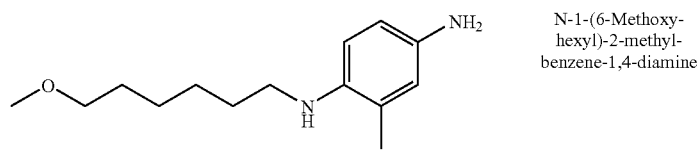 N-1-(6-Methoxy-hexyl)-2-methyl-benzene-1,4-diamine

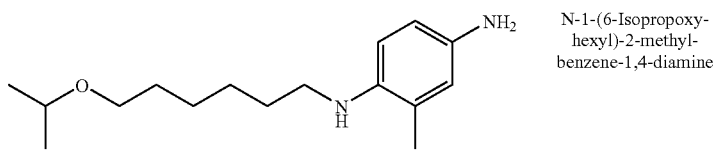 N-1-(6-Isopropoxy-hexyl)-2-methyl-benzene-1,4-diamine

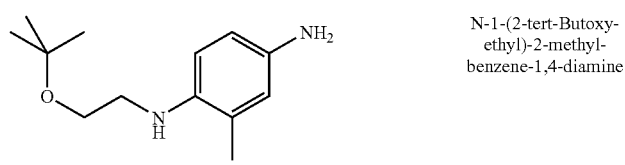 N-1-(2-tert-Butoxy-ethyl)-2-methyl-benzene-1,4-diamine

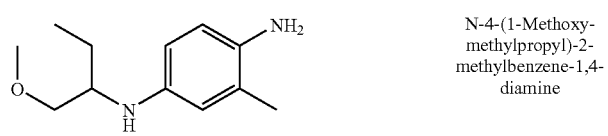 N-4-(1-Methoxy-methylpropyl)-2-methylbenzene-1,4-diamine

-continued

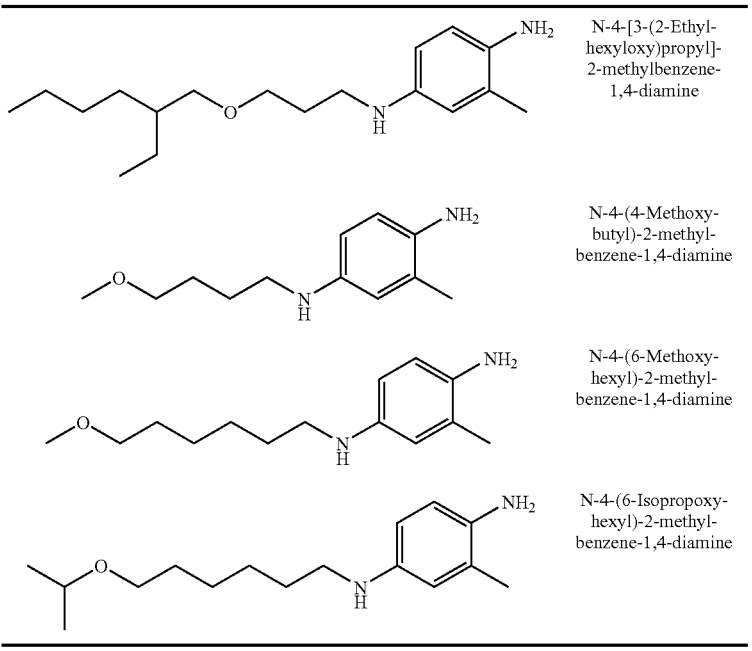

| Structure | Name |
|---|---|
| 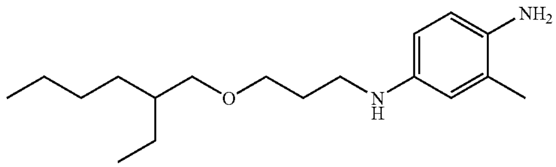 | N-4-[3-(2-Ethyl-hexyloxy)propyl]-2-methylbenzene-1,4-diamine |
| 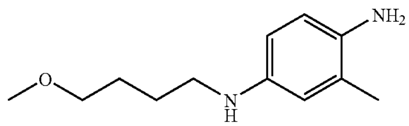 | N-4-(4-Methoxy-butyl)-2-methyl-benzene-1,4-diamine |
| 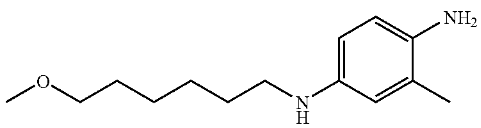 | N-4-(6-Methoxy-hexyl)-2-methyl-benzene-1,4-diamine |
| 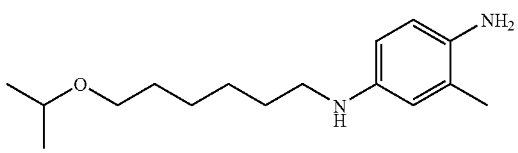 | N-4-(6-Isopropoxy-hexyl)-2-methyl-benzene-1,4-diamine |

In general, the addition salts that can be used for the oxidation bases and the couplers are chosen from acid addition salts, such as hydrochlorides, hydrobromides, sulfates, citrates, succinates, tartrates, lactates, tosylates, benzenesulfonates, phosphates and acetates.

The compounds of formula (I) according to the present disclosure may be prepared according to a method which comprises:
- nucleophilic substitution of the halogen in the para position of the para-halonitrobenzene derivative with a primary amine of formula $RNH_2$ in the presence of a base, R being defined as above;
- reduction of the nitro function of the compound obtained in the preceding step into an amine function, to obtain the compound of formula (I).

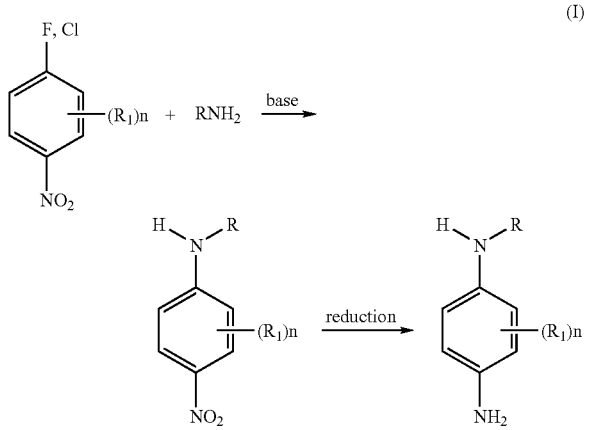

The first step of the synthesis is described in scientific reviews, such as Synthesis 1990 (12), 1147-1148 and Synth. Commun. 1990, 20 (22), 3537-3545.

The second step is a reduction step that may be accomplished with a hydrogenation reaction via heterogeneous catalysis in the presence of Pd/C, Pd(II)/C or Raney Ni, or alternatively by performing a reduction reaction with a metal, such as zinc, iron, tin, etc. (Advanced Organic Chemistry, $4^{th}$ edition, 1992, J. March, Wiley Interscience; Reduction in Organic Chemistry, M. Hudlicky, 1983, Ellis Honwood series Chemical Science).

The present disclosure also concerns the nitro compounds of formula (II) below, and processes for preparing the secondary para-phenylenediamine compounds of formula (I), in which a reduction of the corresponding nitro compound of formula (II) is performed:

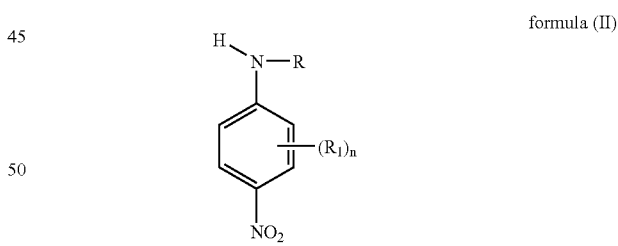

formula (II)

wherein:

R is chosen from a linear (linear $(C_1$-$C_{10})$alkoxy)$(C_4$-$C_{10})$ alkyl radical, a branched (linear $(C_1$-$C_{10})$alkoxy)$(C_3$-$C_{10})$ alkyl radical, a (branched $(C_3$-$C_{10})$alkoxy)$(C_2$-$C_{10})$alkyl radical, and a linear or branched $((C_1$-$C_{10})$alkoxy)$(C_2$-$C_{10})$ alkyl radical substituted with at least one group chosen from hydroxyl, $C_1$-$C_{15}$ alkoxy, amino, mono$(C_1$-$C_{15})$alkylamino, $(C_1$-$C_{15})$alkylcarbonyl, amido, $(C_1$-$C_{15})$alkoxycarbonyl, mono$(C_1$-$C_{15})$alkylaminocarbonyl and di$(C_1$-$C_{15})$alkylaminocarbonyl groups;

$R_1$ is chosen from: a hydrogen atom, a $C_1$-$C_{15}$ alkyl radical, a $C_1$-$C_{15}$alkoxy radical, a $((C_1$-$C_{15})$alkoxy)$C_1$-$C_{15}$alkyl radical, a $C_1$-$C_{15}$ hydroxyalkoxy radical, a $C_1$-$C_{15}$ monohydroxyalkyl radical, a $C_1$-$C_{15}$ polyhydroxyalkyl radical, and a halogen atom; and n is an integer ranging from 1 to 4.

The present disclosure also relates to the use, for the oxidation dyeing of hair, of the above mentioned compound of formula (I) or the addition salt salts thereof The disclosure also relates to a cosmetic composition for dyeing fibers, e.g., human keratin fibers such as hair, comprising, in a medium that is suitable for dyeing, at least one compound of formula (I) as has just been described.

In a non-limiting embodiment, the composition comprises the compound of formula (I) chosen from the following compounds:
— N-(2-Methoxy-1-methylethyl)benzene-1,4-diamine;
— N-(1-Methoxymethylpropyl)benzene-1,4-diamine;
— N-(3-Isopropoxypropyl)benzene-1,4-diamine;
— N-[3-(2-Ethylhexyloxy)propyl]benzene-1,4-diamine;
— 1-(4-Aminophenylamino)-3-methoxypropan-2-ol;
— N-(4-Methoxybutyl)benzene-1,4-diamine;
— N-(5-Methoxypentyl)benzene-1,4-diamine;
— N-(6-Methoxyhexyl)benzene-1,4-diamine;
— N-(6-Ethoxyhexyl)benzene-1,4-diamine;
— N-(6-Isopropoxyhexyl)benzene-1,4-diamine;
— N-(2-Isopropoxyethyl)benzene-1,4-diamine;
— N-(2-tert-Butoxyethyl)benzene-1,4-diamine;
— N-1-(2-Methoxy-1-methylethyl)-2-methylbenzene-1,4-diamine;
— N-1-(1-Methoxymethylpropyl)-2-methylbenzene-1,4-diamine;
— N-1-(3-Isopropoxypropyl)-2-methylbenzene-1,4-diamine;
— N-1-[3-(2-Ethylhexyloxy)propyl]-2-methylbenzene-1,4-diamine;
— 1-(4-Amino-2-methylphenylamino)-3-methoxypropan-2-ol;
— N-1-(4-Methoxybutyl)-2-methylbenzene-1,4-diamine;
— N-1-(5-Methoxypentyl)-2-methylbenzene-1,4-diamine;
— N-1-(6-Methoxyhexyl)-2-methylbenzene-1,4-diamine;
— N-1-(6-Ethoxyhexyl)-2-methylbenzene-1,4-diamine;
— N-1-(6-Isopropoxyhexyl)-2-methylbenzene-1,4-diamine;
— N-1-(2-Isopropoxyethyl)-2-methylbenzene-1,4-diamine;
— N-1-(2-tert-Butoxyethyl)-2-methylbenzene-1,4-diamine;
— N-4-(2-Methoxy-1-methylethyl)-2-methylbenzene-1,4-diamine;
— N-4-(1-Methoxymethylpropyl)-2-methylbenzene-1,4-diamine;
— N-4-(3-Isopropoxypropyl)-2-methylbenzene-1,4-diamine;
— N-4-[3-(2-Ethylhexyloxy)propyl]-2-methylbenzene-1,4-diamine;
-1-(4-Amino-3-methylphenylamino)-3-methoxypropan-2-ol;
— N-4-(4-Methoxybutyl)-2-methylbenzene-1,4-diamine;
— N-4-(5-Methoxypentyl)-2-methylbenzene-1,4-diamine;
— N-4-(6-Methoxyhexyl)-2-methylbenzene-1,4-diamine;
— N-4-(6-Ethoxyhexyl)-2-methylbenzene-1,4-diamine;
— N-4-(6-Isopropoxyhexyl)-2-methylbenzene-1,4-diamine;
— N-4-(2-Isopropoxyethyl)-2-methylbenzene-1,4-diamine;
— N-4-(2-tert-Butoxyethyl)-2-methylbenzene-1,4-diamine;

and the addition salts thereof.

In a non-limiting embodiment, the the compound of formula (I) is present in the composition in an amount ranging from 0.0001% to 20% by weight, such as from 0.005% to 6% by weight, relative to the total weight of the composition.

The medium that is suitable for dyeing may be water or a mixture of water and at least one organic solvent, such as branched or unbranched $C_1$-$C_4$ lower alcohols, such as ethanol and isopropanol; polyols and polyol ethers, for instance 2-butoxyethanol, propylene glycol; propylene glycol monomethyl ether, diethylene glycol monomethyl ether and monoethyl ether, glycerol, and also aromatic alcohols, for instance benzyl alcohol or phenoxyethanol, and mixtures thereof.

The solvents of the medium may be present in amounts ranging from 1% to 40%, such as from 5% to 30%, by weight relative to the total weight of the dye composition.

The cosmetic composition may further comprise at least one cosmetic adjuvant chosen from: antioxidants; penetrating agents; sequestering agents; fragrances; buffers; dispersants; surfactants; conditioning agents; film-forming agents; polymers; ceramides; preserving-agents; nacreous agents; opacifiers; vitamins; or provitamins.

The above adjuvants may be present in an amount for each of them ranging from 0.01% to 20% by weight relative to the weight of the composition.

The composition according to the invention may additionally contain at least one oxidation coupler.

Oxidation couplers that may be mentioned include but are not limited to: meta-phenylenediamines; meta-aminophenols; meta-diphenols; naphthalene-based couplers; heterocyclic couplers; and the addition salts thereof.

Among these oxidation couplers, non-limiting examples that may be mentioned include: 2-methyl-5-aminophenol; 5-N-(β-hydroxyethyl)amino-2-methylphenol; 6-chloro-2-methyl-5-aminophenol; 3-aminophenol; 1,3-dihydroxybenzene (resorcinol); 1,3-dihydroxy-2-methylbenzene; 4-chloro-1,3-dihydroxybenzene; 2,4-diamino-1-(β-hydroxyethyloxy)benzene; 2-amino-4-(β-hydroxyethylamino)-1-methoxybenzene; 1,3-diaminobenzene; 1,3-bis(2,4-diaminophenoxy)propane; 3-ureidoaniline; 3-ureido-1-dimethylaminobenzene; sesamol; 1-β-hydroxyethylamino-3,4-methylenedioxybenzene; α-naphthol; 2-methyl-1-naphthol; 6-hydroxyindole; 4-hydroxyindole; 4-hydroxy-N-methylindole; 2-amino-3-hydroxypyridine; 6-hydroxybenzomorpholine; 3,5-diamino-2,6-dimethoxypyridine; 1-N-(β-hydroxyethyl)amino-3,4-methylenedioxybenzene; 2,6-bis(β-hydroxyethylamino)toluene; and the addition salts thereof.

Generally, the at least one oxidation coupler, if present, may be present in an amount ranging from 0.0001% to 20%, such as from 0.005% to 6%, by weight relative to the total weight of the composition.

The composition according to the invention may further contain at least one additional oxidation base other than the compound of formula (I).

The additional oxidation bases may be chosen from: para-phenylenediamines; bis(phenyl)alkylenediamines; para-aminophenols; ortho-aminophenols; heterocyclic bases; and the addition salts thereof.

Among the para-phenylenediamines, non-limiting mention may be made of: para-phenylenediamine; para-tolylenediamine; 2-chloro-para-phenylenediamine; 2,3-dimethyl-para-phenylenediamine; 2,6-dimethyl-para-phenylenediamine; 2,6-diethyl-para-phenylenediamine; 2,5-dimethyl-para-phenylenediamine; N,N-dimethyl-para-phenylenediamine; N,N-diethyl-para-phenylenediamine; N,N-dipropyl-para-phenylenediamine; 4-amino-N,N-diethyl-3-methylaniline; N,N-bis(β-hydroxyethyl)-para-phenylenediamine; 4-amino-N,N-bis(β-hydroxyethyl)-2-methylaniline; 4-amino-2-chloro-N,N-bis(β-hydroxyethyl)aniline; 2-β-hydroxyethyl-para-phenylenediamine; 2-fluoropara-phenylenediamine; 2-isopropyl-para-phenylenediamine; N-(β-hydroxypropyl)-para-phenylenediamine; 2-hydroxymethyl-para-phenylenediamine; N,N-dimethyl-3-methyl-para-phenylenediamine; N-ethyl-N-(β-hydroxyethyl)-para-phenylenediamine; N-(β,γ-di-hydroxypropyl)-para-phenylenediamine; N-(4'-aminophenyl)-para-phenylenediamine; N-phenyl-para-phenylenediamine; 2-β-hydroxyethyloxy-para-phenylenediamine; 2-β-acetylaminoethyloxy-para-phenylenediamine; N-(β-methoxyethyl)-para-phenylenediamine; 4-aminophenylpyrrolidine; 2-thienyl-para-phenylenediamine; 2-β-hydroxyethylamino-5-aminotoluene; 3-hydroxy-1-(4'-aminophenyl)pyrrolidine; 6-(4-aminophenylamino) hexan-1-ol; and the acid addition salts thereof.

In some embodiments, the at least one additional oxidation base is chosen from, para-phenylenediamines chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the acid addition salts thereof Among the bis(phenyl)alkylenediamines, non-limiting mention may be made, by way of example, of: N,N'-bis(β-hydroxyethyl)-N,N'-bis(4'-aminophenyl)-1,3-diaminopropanol; N,N'-bis(β-hydroxyethyl)-N,N'-bis(4'-aminophenyl) ethylenediamine; N,N'-bis(4-aminophenyl) tetramethylenediamine; N,N'-bis(β-hydroxyethyl)-N,N'-bis (4-amino-phenyl)tetramethylenediamine; N,N'-bis(4-methylaminophenyl)tetramethylenediamine; N,N'-bis (ethyl)-N,N'-bis(4'-amino-3'-methylphenyl) ethylenediamine; 1,8-bis(2,5-diamino-phenoxy)-3,6-dioxaoctane; and the acid addition salts thereof.

Among the para-aminophenols, non-limiting mention may be made, by way of example, of: para-aminophenol; 4-amino-2-methylphenol; 4-amino-3-methylphenol; 4-amino-3-fluorophenol; 4-amino-3-chlorophenol; 4-amino-3-hydroxymethylphenol; 4-amino-2-methylphenol; 4-amino-2-hydroxymethylphenol; 4-amino-2-methoxymethylphenol; 4-amino-2-aminomethylphenol; 4-amino-2-(β-hydroxyethyl-aminomethyl)phenol; 4-amino-2-fluorophenol; 4-amino-2,6-dichlorophenol; 4-amino-6[((5'-amino-2'-hydroxy-3'-methyl)phenyl)methyl]-2-methylphenol; bis(5'-amino-2'-hydroxy)phenylmethane; and the acid addition salts thereof.

Among the ortho-aminophenols, non-limiting mention may be made, by way of example, of: 2-aminophenol; 2-amino-5-methylphenol; 2-amino-6-methylphenol; 5-acetamido-2-aminophenol; and the acid addition salts.

Among the heterocyclic bases, non-limiting mention may be made, by way of example, of: pyridine derivatives; pyrimidine derivatives; and pyrazole derivatives.

Non-limiting examples of suitable pyridine derivative include the compounds described, for example, in patents GB 1 026 978 and GB 1 153 196, as well as 2,5-diaminopyridine, 2-(4-methoxyphenyl)amino-3-aminopyridine, 3,4-diaminopyridine, and the acid addition salts thereof.

Other non-limiting examples of pyridine oxidation bases that may be used in the present disclosure include the 3-aminopyrazolo[1,5-a]pyridine oxidation bases or the addition salts thereof described, such as those described in French Patent application FR 2801308 including: pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyridine-6-ol; and 3-aminopyrazolo[1,5-a]pyrid-7-ol; and the acid addition salts thereof.

Among the pyrimidine derivatives, non-limiting mention may be made of the compounds described in patents DE 23 59 399; JP 88169571; JP 0563124; EP 0 770 375, or patent application WO 96/15765, such as: 2,4,5,6-tetraaminopyrimidine; 4-hydroxy-2,5,6-triaminopyrimidine; 2-hydroxy-4,5,6-triaminopyrimidine; 2,4-dihydroxy-5,6-diaminopyrimidine; 2,5,6-triaminopyrimidine; the acid addition salts thereof; and the tautomeric forms thereof when tautomeric equilibrium exists.

Among the pyrazole derivatives, non-limiting mention may be made of the compounds described in patents DE 38 43 892, DE 41 33 957 and patent applications WO 94/08969, WO 94/08970, FR-A-2 733749 and DE 195 43 988, including: 4,5-diamino-1-methylpyrazole; 4,5-diamino-1-(β-hydroxyethyl)pyrazole; 3,4-diaminopyrazole; 4,5-diamino-1-(4'-chlorobenzyl)pyrazole; 4,5-diamino-1,3-dimethylpyrazole; 4,5-diamino-3-methyl-1-phenylpyrazole; 4,5-diamino-1-methyl-3-phenylpyrazole; 4-amino-1,3-dimethyl-5-hydrazinopyrazole; 1-benzyl-4,5-diamino-3-methylpyrazole; 4,5-diamino-3-tert-butyl-1-methylpyrazole; 4,5-diamino-1-tert-butyl-3-methylpyrazole; 4,5-diamino-1-(β-hydroxyethyl)-3-methylpyrazole; 4,5-diamino-1-ethyl-3-methylpyrazole; 4,5-diamino-1-ethyl-3-(4'-methoxyphenyl) pyrazole; 4,5-diamino-1-ethyl-3-hydroxymethylpyrazole; 4,5-diamino-3-hydroxymethyl-1-methylpyrazole; 4,5-diamino-3-hydroxymethyl-1-isopropylpyrazole; 4,5-diamino-3-methyl-1-isopropylpyrazole; 4-amino-5-(2'-aminoethyl) amino-1,3-dimethylpyrazole; 3,4,5-triaminopyrazole; 1-methyl-3,4,5-triaminopyrazole; 3,5-diamino-1-methyl-4-methylaminopyrazole; 3,5-diamino-4-(β-hydroxyethyl) amino-1-methylpyrazole; and the addition salts thereof.

Generally, if present, the at least one additional oxidation base is present in an amount ranging from 0.0001% to 20% by weight, such as from 0.005% to 6% by weight, relative to the total weight of the composition.

Addition salts that can be used for the oxidation bases and the couplers include acid addition salts, such as: hydrochlorides; hydrobromides; sulfates; citrates; succinates; tartrates; lactates; tosylates; benzenesulfonates; phosphates; and acetates.

The dye composition in accordance with the present disclosure may also contain at least one direct dye, which may be chosen from: neutral, acidic or cationic nitrobenzene dyes; neutral, acidic or cationic azo direct dyes; neutral, acidic or cationic quinone, such as anthraquinone direct dyes; azine direct dyes; methine, azomethine, triarylmethane or indoamine direct dyes; and natural direct dyes. In one non-limiting aspect of the present disclosure, the composition according to the invention comprises at least one direct dye chosen from cationic direct dyes and natural direct dyes.

Among the cationic direct dyes that may be used according to the present disclosure, mention may be made of the cationic azo direct dyes described in patent applications WO 95/15144, WO 95/01772 and EP 714 954, such as: 1,3-dimethyl-2-[[4-(dimethylamino)phenyl]azo]-1H-imidazolium chloride; 1,3-dimethyl-2-[(4-aminophenyl)azo]-1H-imidazolium chloride; and 1-methyl-4-[(methylphenylhydrazono)methyl]pyridinium methyl sulfate.

Among the natural direct dyes that may be used according to the present disclosure, mention may be made of: lawsone; juglone; alizarin; purpurin; carminic acid; kermesic acid; purpurogallin; protocatechaldehyde; indigo; isatin; curcumin; spinulosin; and apigenidin. Extracts or decoctions containing these natural dyes, such as henna-based poultices or extracts, may be used.

In one non-limiting embodiment, the at least one direct dye may be contained in an amount from 0.001% to 20% by weight, such as from 0.005% to 10% by weight, relative to the total weight of the ready-to-use composition.

A ready-to-use dye composition of the present disclosure may be obtained by adding at least one oxidizing agent conventionally used for the oxidation dyeing of keratin fibers such as, for example, hydrogen peroxide, urea peroxide, alkali metal bromates, persalts such as perborates and persulfates, peracids and oxidase enzymes. Of these oxidizing agents, mention may be made of: hydrogen peroxide; peroxidases; two-electron oxidoreductases such as uricases; and four-electron oxygenases, for instance laccases. In one embodiment, hydrogen peroxide is used.

The above examples are non-limiting. One of ordinary skill in the art would know to take care to select the adjuvant(s), additional oxidation dye precursor(s), oxidation coupler(s), and direct dye(s) such that the advantageous properties intrinsically associated with the presently disclosed oxidation dye composition are not, or are not substantially, adversely affected by the envisaged addition(s).

The pH of the dye composition in accordance with the present disclosure may be from 3 to 12, such as from 5 to 11. The pH may be adjusted to a desired value using acidifying or basifying agents that usually used in the dyeing of keratin fibers, or by using standard buffer systems.

Among the acidifying agents that may be mentioned, for example, are mineral or organic acids other than carboxylic diacids, such as: hydrochloric acid; orthophosphoric acid; and sulfuric acid; carboxylic acids such as acetic acid, tartaric acid, citric acid, lactic acid; and sulfonic acids.

Among the basifying agents that may be mentioned, for example, are aqueous ammonia; alkali metal carbonates; alkanolamines such as monoethanolamine, diethanolamine and triethanolamine and derivatives thereof; sodium hydroxide; potassium hydroxide; and the compounds of formula:

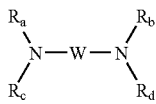

wherein W is a propylene residue optionally substituted with a hydroxyl group or a $C_1$-$C_4$ alkyl radical; and $R_a$, $R_b$, $R_c$ and $R_d$, which may be identical or different, represent a hydrogen atom; a $C_1$-$C_4$ alkyl; or $C_1$-$C_4$ hydroxyalkyl radical.

The dye composition according to the present disclosure may be in various forms, such as a liquid, a cream, a gel, or in any other form that is suitable for dyeing keratin fibers.

Another aspect of the present disclosure relates to a process in which the composition as described above is applied to the fibers and the color is developed using an oxidizing agent. The color may be developed at acidic, neutral or alkaline pH. The oxidizing agent may be added to the composition of the invention just at the time of use. Further, the oxidizing agent may be present in an oxidizing composition that is applied simultaneously with or sequentially to the composition of the invention.

According to one particular embodiment, the composition according to the present, disclosure is mixed, for example at the time of use, with a composition containing, in a medium that is suitable for dyeing, at least one oxidizing agent, wherein the oxidizing agent is present in an amount that is sufficient to develop a desired coloration. The resultant mixture is then applied to the keratin fibers. After an action time of 3 to 50 minutes, for example 5 to 30 minutes, the keratin fibers are rinsed, washed with shampoo, rinsed again, and then dried.

The oxidizing composition may contain various adjuvants conventionally used in hair dye compositions and as defined above.

The pH of the oxidizing composition containing the oxidizing agent is such that, after mixing with the dye composition, the pH of the resulting composition applied to the keratin fibers may range from 3 to 12, such as from 5 to 11. The pH of the oxidizing composition may be adjusted to a desired value through the use of acidifying or basifying agents that are typically used in the dyeing of keratin fibers and as described above.

The ready-to-use composition that is finally applied to the keratin fibers may be in various forms, such as in the form of a liquid, a cream, a gel, or any other form that is suitable for dyeing keratin fibers.

The present disclosure also relates to the use of the cosmetic composition comprising, in a medium that is suitable for dyeing, at least one compound of formula (I) for dyeing fibers, such as hair.

A further aspect of the present disclosure is a multi-compartment device or dyeing "kit", in which a first compartment contains the dye composition described above and a second compartment contains an oxidizing composition. This device may be equipped with a means for applying the desired mixture to hair, such as the devices described in patent FR-2 586 913.

Using this device, it is possible to dye keratin fibers via a process that includes mixing a dye composition in accordance with the invention with an oxidizing agent as described above, and applying the resultant mixture to the keratin fibers for a time that is sufficient to develop a desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurement.

The examples that follow serve to illustrate the invention without, however, being limiting in nature.

EXAMPLES

Example 1

Synthesis of
N-(2-methoxy-1-methylethyl)benzene-1,4-diamine
dihydrochloride (2)

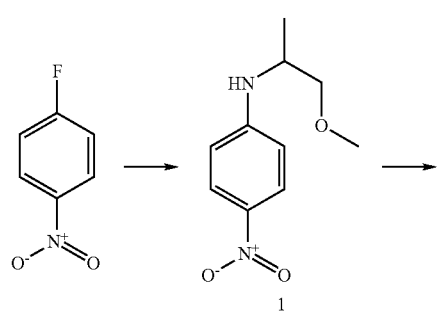

Step 1: Preparation of (2-methoxy-1-methylethyl)(4-nitrophenyl)amine (1)

21 g (0.15 mol) of 1-fluoro-4-nitrobenzene and 42 ml of 2-amino-1-methoxypropane were introduced into a 150 ml three-necked flask. The mixture was stirred for 15 minutes and brought to the boiling point. After reaction for 2 to 3 hours, the reaction medium was poured onto ice. A yellow precipitate formed. This precipitate was filtered off, washed with water, and then successively washed with a minimum amount of ethanol, isopropyl ether, and petroleum ether. 27.8 g of expected product were isolated.

|   | THEORY | FOUND |
|---|--------|-------|
| C | 57.13  | 56.94 |
| H | 6.71   | 6.70  |
| N | 13.32  | 13.04 |
| O | 22.83  | 22.80 |

Step 2: Preparation of N-(2-methoxy-1-methylethyl)benzene-1,4-diamine dihydrochloride (2)

21 g (0.1 mol) of (1) were placed in a mixture of 42 ml of 96° alcohol. 42 ml of cyclohexene and 4.4 ml of water. 4.2 g of 10% palladium-on-charcoal were added thereto. The mixture was refluxed for 2 hours. The catalyst was filtered off and then washed with ethanol. The filtrate was concentrated to dryness and then dissolved in 40 ml of absolute ethanol. This solution was cooled to −10° C. and 50 ml of 7N hydrochloric ethanol was added. A white precipitate formed and was filtered off at 0° C. and then washed successively with ethanol, acetone, isopropyl ether and petroleum ether. 2.5 g of expected product were obtained.

|    | THEORY | FOUND |
|----|--------|-------|
| C  | 47.43  | 47.30 |
| H  | 7.11   | 7.12  |
| N  | 11.07  | 10.94 |
| O  | 6.32   | 6.57  |
| Cl | 28.06  | 28.06 |

The proton NMR and mass spectra were in accordance with the expected structure of the product.

Example 2

Synthesis of
N-(1-methoxymethylpropyl)benzene-1,4-diamine
dihydrochloride (4)

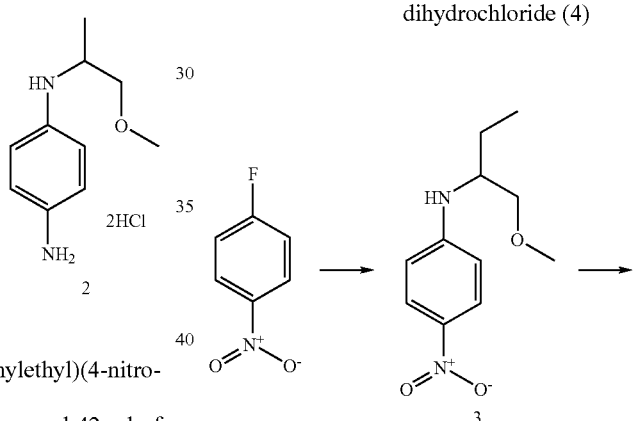

Step 1: Preparation of (1-methoxymethylpropyl)(4-nitro-)amine (3)

23 g of 1-methoxymethylpropylamine was added to 11.3 g (0.08 mol) of 1-fluoro-4-nitrobenzene. The mixture was refluxed for 6 hours and was then poured onto ice. A yellow precipitate formed; this precipitate was filtered off and washed with water, with a minimum amount of ethanol, with isopropyl ether, and then with petroleum ether. After the precipitate was dried, 15 g of a yellow solid were obtained.

|   | THEORY | FOUND |
|---|--------|-------|
| C | 58.91  | 58.81 |
| H | 7.19   | 7.22  |
| N | 12.49  | 12.46 |
| O | 21.40  | 21.31 |

Step 2: Preparation of N-(1-methoxymethylpropyl)benzene-1,4-diamine dihydrochloride (4)

0.1 mol of (3) (22.4 g) was placed in a mixture of 42 ml of 96° alcohol, 42 ml of cyclohexene and 4.4 ml of water. 4.2 g of 10% palladium-on-charcoal was added thereto. The mixture was refluxed for 2 hours. The catalyst was filtered off and washed with alcohol. The filtrate was concentrated to dryness and then dissolved in 40 ml of absolute ethanol. This solution was cooled to −10° C. and 50 ml of 7N hydrochloric ethanol was added. A white precipitate formed. This precipitate was filtered off at 0° C. and then washed successively with ethanol, acetone, isopropyl ether and finally petroleum ether. 2.4 g of product were obtained.

|    | THEORY, H$_2$O | FOUND |
|----|----------------|-------|
| C  | 46.32          | 46.42 |
| H  | 7.77           | 7.75  |
| N  | 9.82           | 9.86  |
| O  | 10.22          | 10.53 |
| Cl | 24.86          | 25.43 |

The proton NMR and mass spectra were in accordance with the expected structure of the product.

Example 3

Synthesis of N-(3-isopropoxypropyl)benzene-1,4-diamine dihydrochloride (6)

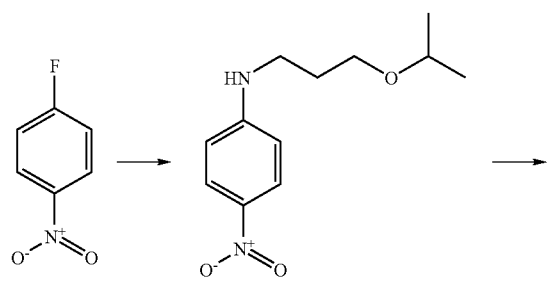

5

-continued

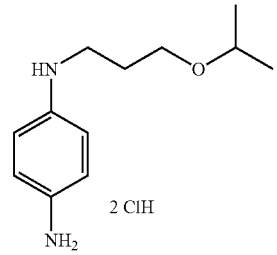

6

Step 1: Preparation of (3-isopropoxypropyl)(4-nitrophenyl)amine (5)

42 ml of 3-isopropoxypropylamine was added to 21 g (0.15 mol) of 1-fluoro-4-nitrobenzene. As the reaction is exothermic, the temperature was maintained at 90° C. by cooling slightly. After 30 minutes, the reaction was complete. The medium was poured onto ice, and an oil appeared. This oil was extracted with ethyl acetate, and the organic phase is washed with water and dried over sodium sulfate. After the oil was evaporated to dryness, 35 g of a yellow oil were obtained.

|   | THEORY | FOUND |
|---|--------|-------|
| C | 60.49  | 59.61 |
| H | 7.61   | 7.66  |
| N | 11.76  | 11.74 |
| O | 20.14  | 20.64 |

Step 2: Preparation of N-(3-isopropoxypropyl)benzene-1,4-diamine dihydrochloride (6)

0.1 mol of (5) (23.8 g) was placed in a mixture of 50 ml of 96° alcohol, 50 ml of cyclohexene and 4.8 ml of water. 4.8 g of 10% palladium-on-charcoal was added thereto. The resultant mixture was refluxed for 2 hours. The catalyst was filtered off and the filtrate was concentrated to dryness. Then, the filtrate was dissolved in 40 ml of absolute ethanol. This solution was cooled to −10° C., and 50 ml of 7N hydrochloric ethanol was added thereto. A white precipitate formed, and was filtered off at 0° C. The white precipitate was then washed successively with ethanol, acetone, isopropyl ether and petroleum ether. 2.8 g of product were isolated.

|    | THEORY | FOUND |
|----|--------|-------|
| C  | 51.25  | 51.16 |
| H  | 7.83   | 7.91  |
| N  | 9.96   | 9.87  |
| O  | 5.69   | 5.94  |
| Cl | 25.27  | 25.33 |

The proton NMR and mass spectra were in accordance with the expected structure of the product.

Example 4

Synthesis of N-(2-isopropoxyethyl)benzene-1,4-diamine dihydrochloride (8)

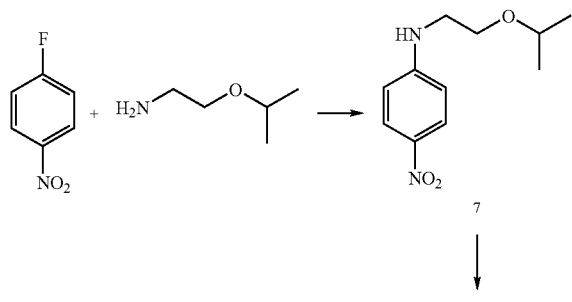

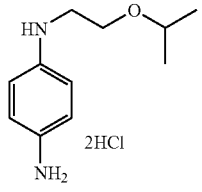

Step 1: Synthesis of N-(2-isopropoxyethyl)-4-nitro-1-aminobenzene (7)

2 g of para-fluoronitrobenzene was added to a solution of 20 ml of N-methylpyrrolidinone (NMP), 1.75 g of 2-aminoethyl isopropyl ether and 2.35 g of $K_2CO_3$. The reaction medium was heated at 60° C. for 8 hours and, after cooling to room temperature, was poured into a water+ice mixture. A yellow precipitate formed and was filtered off. The precipitate was reslurried in water and then dried over $P_2O_5$. 2.57 g of N-(2-isopropoxyethyl)-4-nitro-1-aminobenzene (7) were obtained.

Step 2: Synthesis of N-(2-isopropoxyethyl)benzene-1,4-diamine dihydrochloride (8)

The N-(2-isopropoxyethyl)-4-nitro-1-aminobenzene (7) obtained above was reduced with a boiling zinc/ammonium chloride/water/ethanol mixture. The corresponding amine was isolated in dihydrochloride form.

The proton NMR and mass spectra were in accordance with the expected structure of the product.

Example 5

Synthesis of N-[3-(2-ethylhexyloxy)propyl]benzene-1,4-diamine (10)

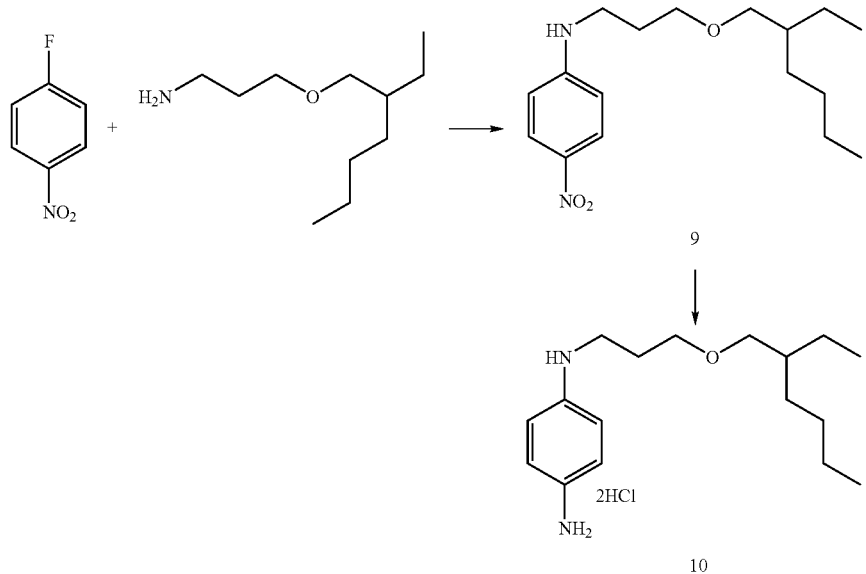

Step 1: Synthesis of N-{3-[(2-ethylhexyl)oxy]propyl}-N-(4-nitrophenyl)amine (9):

2 g of para-fluoronitrobenzene was added to a solution of 20 ml of N-methylpyrrolidinone, 3.19 g of 2-ethylhexyl 3-aminopropyl ether and 2.35 g of $K_2CO_3$. The reaction medium was heated at 60° C. for 10 hours and, after it was cooled to room temperature, poured into a water+ice mixture. The resulting medium was extracted with ethyl acetate, and the organic phase was then concentrated by evaporating under vacuum. 2.73 g of N-[2-(3-ethylheptyloxy)ethyl]-4-nitro-1-aminobenzene (9) were obtained.

Step 2: Synthesis of N-[3-(2-ethylhexyloxy)propyl]benzene-1,4-diamine (10):

The N-[2-(3-ethylheptyloxy)ethyl]-4-nitro-1-aminobenzene (9) obtained above was reduced with a boiling zinc/ ammonium chloride/water/ethanol mixture. The corresponding amine was isolated in dihydrochloride form.

The proton NMR and mass spectra were in accordance with the expected structure of the product.

Example 6

Synthesis of N-(4-amino-2-methoxyphenyl)-N-(3-isopropoxypropyl)-amine dihydrochloride (12)

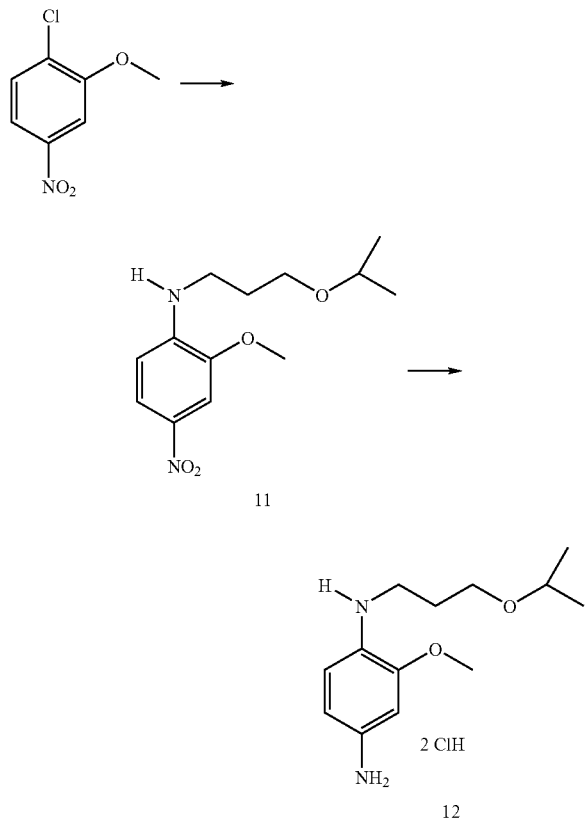

Step 1: Preparation of N-(3-isopropoxypropyl)-N-(2-methoxy-4-nitrophenyl)amine (11)

1.87 g (0.01 mol) of 2-chloro-5-nitroanisole, 1.2 g (0.022 mol) of sodium carbonate, 1.3 g (0.012 mol) of 3-isopropoxypropylamine and 10 ml of NMP were introduced into a three-necked flask under nitrogen. The mixture was heated to 100° C. After reaction for 3 days, the reaction mixture was cooled and 35 ml of distilled water were added slowly with vigorous stirring. The nitro derivative appeared in the form of a brown semi-solid, and was extracted with dichloromethane and purified on a column of silica, eluting with ⅔ ethyl acetate/heptane. 1.5 g of expected nitro derivative were obtained in the form of an orange solid.

The proton and $^{13}C$ NMR spectra were in accordance with the expected structure of the product.

Step 2: Preparation of N-(4-amino-2-methoxyphenyl)-N-(3-isopropoxypropyl)amine dihydrochloride (12)

The N-(3-isopropoxypropyl)-N-(2-methoxy-4-nitrophenyl)amine (11) obtained above was reduced with a boiling zinc/ammonium chloride/water/ethanol mixture. The corresponding amine was isolated in dihydrochloride form.

The proton NMR and mass spectra were in accordance with the expected structure of the product.

Example 7

Synthesis of 1-[(4-aminophenyl)amino]-3-methoxypropan-2-ol hydrochloride (14)

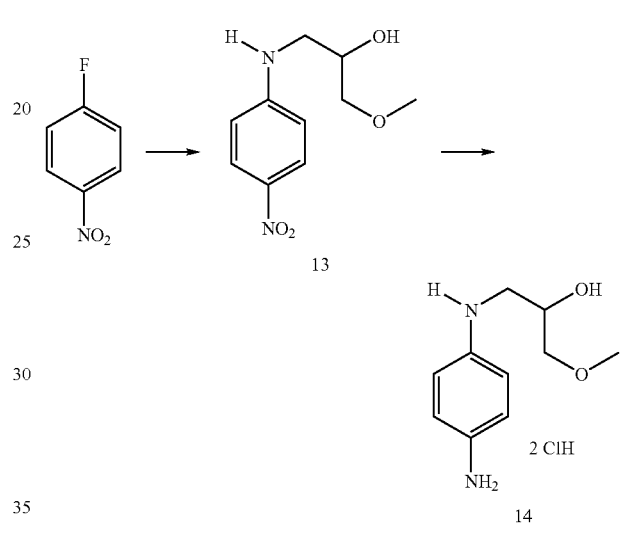

Step 1: Preparation of 1-methoxy-3-[(4-nitrophenyl)amino]propan-2-ol (13)

2.82 g (0.02 mol) of 1-fluro-4-nitrobenzene, 2.65 g (0.025 mol) of sodium carbonate and 5 ml of NMP were introduced into a three-necked flask under nitrogen. The mixture was stirred. 2.31 g (0.022 mol) of 1-amino-3-methoxypropan-2-ol in 10 ml of NMP were then added dropwise. This mixture was heated to 70° C. After reacting for 24 hours, the reaction mixture was cooled and 50 ml of distilled water were then added slowly with vigorous stirring. The nitro derivative appeared in the form of a yellow semi-solid, and was extracted with dichloromethane. The organic phase was evaporated under vacuum until all of the NMP was removed. 15 ml of distilled water were added to the yellow oil that was obtained. A yellow precipitate formed. This precipitate was filtered off, washed several times with water and then with pentane, and dried under vacuum. 2.9 g of expected nitro derivative were obtained in the form of a yellow powder.

Step 2: Preparation of 1-[(4-aminophenyl)amino]-3-methoxypropan-2-ol dihydrochloride (14)

The 1-methoxy-3-[(4-nitrophenyl)amino]propan-2-ol (13) obtained above was reduced with a boiling zinc/ammonium chloride/water/ethanol mixture. The corresponding amine was isolated in dihydrochloride form.

The proton NMR and mass spectra were in accordance with the expected structure of the product.

Example 8

Synthesis of N-(4-aminophenyl)-N-(6-methoxyhexyl)amine dihydrochloride (17)

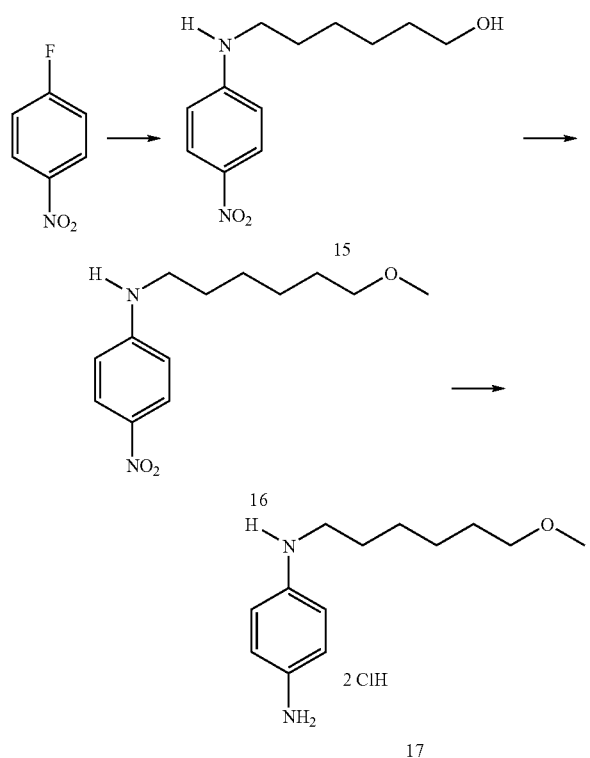

Step 1: Preparation of 6-[(4-nitrophenyl)amino]hexan-1-ol (15)

2.82 g (0.02 mol) of 1-fluoro-4-nitrobenzene, 2.65 g (0.025 mol) of sodium carbonate and 5 ml of NMP were introduced into a three-necked flask under nitrogen. The mixture was stirred and 2.55 g (0.022 mol) of 1-amino-3-methoxypropan-2-ol in 15 ml of NMP were then added dropwise. This mixture was heated to 70° C. After reacting for 24 hours, the reaction mixture was cooled and 50 ml of distilled water were then added slowly with vigorous stirring. A yellow precipitate formed. This precipitate was filtered off, washed several times with water, and then with pentane. The precipitate was then dried under vacuum. 4.45 g of expected nitro derivative were obtained in the form of a yellow powder.

Step 2: Preparation of N-(6-methoxyhexyl)-N-(4-nitrophenyl)amine (16)

1.19 g (0.005 mol) of the nitro derivative obtained above, and 7 ml of 1,4-dioxane were introduced into a three-necked flask under nitrogen. The mixture was heated to 65° C. and 1 g of potassium hydroxide (85%) was then introduced. At this temperature, 1 equivalent of dimethyl sulfate was added very slowly (1 drop per minute). Heating was continued with stirring for 2 hours. The reaction mixture was cooled, filtered, and then washed with dichloromethane. The yellow filtrate obtained was washed twice with water. The organic phase was dried and then evaporated under vacuum. 1.3 g of expected nitro derivative were obtained in the form of a viscous yellow product.

Step 3: Preparation of N-(4-aminophenyl)-N-(6-methoxyhexyl)amine dihydrochloride (17)

The N-(6-methoxyhexyl)-N-(4-nitrophenyl)amine (16) obtained above was reduced with a boiling zinc/ammonium chloride/water/ethanol mixture. The corresponding amine was isolated in dihydrochloride form.

The proton NMR and mass spectra were in accordance with the expected structure of the product.

EXAMPLES OF DYEING

Examples 1 to 13

Dye Composition Using N-(2-methoxy-1-methyl)-1,4-diamine dihydrochloride (2)

Examples 1 to 7

Dyeing in Acidic Medium

The following dye compositions were prepared:

| | Example | | | | | | |
|---|---|---|---|---|---|---|---|
| | 1 | 2 | 3 | 4 | 5 | 6 | 7 |
| N-(2-Methoxy-1-methylethyl)benzene-1,4-diamine dihydrochloride (2) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |

-continued

| Dye support (1) | (*) | (*) | (*) | (*) | (*) | (*) | (*) |
|---|---|---|---|---|---|---|---|
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again, and then dried.

The shades obtained are given in the table below:

| | Example | | | | | | |
|---|---|---|---|---|---|---|---|
| | 1 | 2 | 3 | 4 | 5 | 6 | 7 |
| Shade observed | grey | strong violet | strong red-violet grey | strong violet-grey | violet-grey | strong blue | strong blue-violet |

Examples 8 to 13

Dyeing in Basic Medium

The following dye compositions were prepared:

| | Example | | | | | |
|---|---|---|---|---|---|---|
| | 8 | 9 | 10 | 11 | 12 | 13 |
| N-(2-Methoxy-1-methyl-ethyl)benzene-1,4-diamine dihydrochloride (2) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo[5,1-c]-[1,2,4]triazole | | | | $10^{-3}$ mol | | |
| 2-(2,4-Diaminophenoxy)ethanol hydrochloride | | | | | $10^{-3}$ mol | |
| 3-Amino-2-chloro-6-methylphenol hydrochloride | | | | | | $10^{-3}$ mol |
| Dye support (2) | (*) | (*) | (*) | (*) | (*) | (*) |
| Demineralized water qs | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

|  | Example | | | | | |
|---|---|---|---|---|---|---|
|  | 8 | 9 | 10 | 11 | 12 | 13 |
| Shade observed | strong violet | red-brown | red-brown | chromatic red-violet | strong blue | strong blue-violet |

Examples 14 to 27

Dye Composition Using N-(1-methoxymethylpropyl)benzene-1,4-diamine dihydrochloride (4)

Examples 14 to 20

Dyeing in Acidic Medium

The following dye compositions were prepared:

|  | Example | | | | | | |
|---|---|---|---|---|---|---|---|
|  | 14 | 15 | 16 | 17 | 18 | 19 | 20 |
| N-(1-Methoxymethyl-propyl)benzene-1,4-diamine dihydrochloride (4) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 14 | 15 | 16 | 17 | 18 | 19 | 20 |
| Shade observed | strong blue-grey | strong violet | strong red-violet grey | strong violet-grey | strong blue-violet grey | strong blue | strong blue-violet |

Examples 21 to 27

Dyeing in Basic Medium

The following dye compositions were prepared:

| | Example | | | | | | |
|---|---|---|---|---|---|---|---|
| | 21 | 22 | 23 | 24 | 25 | 26 | 27 |
| N-(1-Methoxymethyl-propyl)benzene-1,4-diamine dihydrochloride (4) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy) ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

| | Example | | | | | | |
|---|---|---|---|---|---|---|---|
| | 21 | 22 | 23 | 24 | 25 | 26 | 27 |
| Shade observed | brown | violet | red | red-grey | chromatic red-violet | strong chromatic blue | strong blue-violet |

Examples 28 to 41

Dye Composition Using N-(3-isopropoxypropyl)-benzene-1,4-diamine dihydrochloride (6)

Examples 28 to 34

Dyeing in Acidic Medium

The following dye compositions were prepared:

| | Example | | | | | | |
|---|---|---|---|---|---|---|---|
| | 28 | 29 | 30 | 31 | 32 | 33 | 34 |
| N-(3-Isopropoxypropyl)-benzene-1,4-diamine dihydrochloride (6) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |

-continued

| | | | | | | | |
|---|---|---|---|---|---|---|---|
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

| | Example | | | | | | |
|---|---|---|---|---|---|---|---|
| | 28 | 29 | 30 | 31 | 32 | 33 | 34 |
| Shade observed | strong grey | strong violet | strong violet-grey | strong violet-grey | strong red-violet | strong blue | strong blue-violet |

Examples 35 to 41

Dyeing in Basic Medium

The following dye compositions were prepared:

| | Example | | | | | | |
|---|---|---|---|---|---|---|---|
| | 35 | 36 | 37 | 38 | 39 | 40 | 41 |
| N-(3-Isopropoxy-propyl)benzene-1,4-diamine dihydrochloride (6) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methyl-phenol | | $10^{-3}$ mol | | | | | |
| 1H-Indol-6-ol | | | $10^{-3}$ mol | | | | |
| 2-Aminopyridin-3-ol | | | | $10^{-3}$ | | | |
| 3,6-Dimethyl-1H-pyrazolo[5,1-c]-[1,2,4]triazole | | | | | $10^{-3}$ mol | | |
| 2-(2,4-Diamino-phenoxy)ethanol hydrochloride | | | | | | $10^{-3}$ mol | |
| 3-Amino-2-chloro-6-methylphenol hydrochloride | | | | | | | $10^{-3}$ mol |

-continued

| | | | | | | | |
|---|---|---|---|---|---|---|---|
| Dye support (2) | (*) | (*) | (*) | (*) | (*) | (*) | (*) |
| Demineralized water qs | 100 g | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

| | Example | | | | | |
|---|---|---|---|---|---|---|
| 35 | 36 | 37 | 38 | 39 | 40 | 41 |
| Shade observed: brown | strong violet | strong red-violet grey | red-grey | chromatic red-violet | strong blue | strong blue-violet |

Examples 42 to 55

Dye Composition Using N-(2-isopropoxyethyl)benzene-1,4-diamine dihydrochloride (8)

Examples 42 to 48

Dyeing in Acidic Medium

The following dye compositions were prepared:

| | Example | | | | | | |
|---|---|---|---|---|---|---|---|
| | 42 | 43 | 44 | 45 | 46 | 47 | 48 |
| N-(2-Isopropoxyethyl)benzene-1,4-diamine dihydrochloride (8) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 42 | 43 | 44 | 45 | 46 | 47 | 48 |
| Shade observed | strong brown | strong red-violet grey | strong brown | strong red-brown | strong red-brown | strong blue | strong violet |

Examples 49 to 55

Dyeing in Basic Medium

The following dye compositions were prepared:

|  | Example | | | | | | |
|---|---|---|---|---|---|---|---|
|  | 49 | 50 | 51 | 52 | 53 | 54 | 55 |
| N-(2-Isopropoxyethyl)benzene-1,4-diamine dihydrochloride (8) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 49 | 50 | 51 | 52 | 53 | 54 | 55 |
| Shade observed | orange-brown | red-violet | orange | red | red | strong blue | strong blue-violet |

Examples 56 to 69

Dye Composition Using N-[3-(2-ethylhexyloxy)propyl]benzene-1,4-diamine (10)

Examples 56 to 62

Dyeing in Acidic Medium

The following dye compositions were prepared:

|  | Example | | | | | | |
|---|---|---|---|---|---|---|---|
|  | 56 | 57 | 58 | 59 | 60 | 61 | 62 |
| N-[3-(2-Ethylhexyloxy)propyl]-benzene-1,4-diamine (10) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

| | Example | | | | | | |
|---|---|---|---|---|---|---|---|
| | 56 | 57 | 58 | 59 | 60 | 61 | 62 |
| Shade observed | strong brown | strong violet-grey | strong grey | strong brown | strong red-brown | strong blue-violet grey | strong violet-grey |

Examples 63 to 69

Dyeing in Basic Medium

The following dye compositions were prepared:

|  | Example | | | | | | |
|---|---|---|---|---|---|---|---|
|  | 63 | 64 | 65 | 66 | 67 | 68 | 69 |
| N-[3-(2-Ethylhexyloxy)propyl]-benzene-1,4-diamine (10) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

| (*): dye support (2) pH 9.5 | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 63 | 64 | 65 | 66 | 67 | 68 | 69 |
| Shade observed | strong brown | strong red-violet grey | strong red-brown | strong red-brown | strong red | strong blue-violet grey | strong violet |

What is claimed is:

1. A compound, wherein the compound is chosen from secondary para-phenylenediamines of formula (I) and the addition salts thereof:

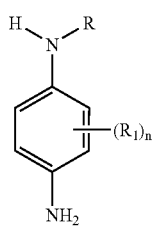

(I)

wherein:

R is chosen from: a linear (linear ($C_1$-$C_{10}$)alkoxy)($C_5$-$C_{10}$) alkyl radical; a branched (linear ($C_1$-$C_{10}$)alkoxy)($C_3$-$C_{10}$)alkyl radical; a (branched ($C_3$-$C_{10}$)alkoxy)($C_2$-$C_{10}$) alkyl radical; and a linear or branched (($C_1$-$C_{10}$)alkoxy) ($C_2$-$C_{10}$)alkyl radical substituted with at least one group chosen from hydroxyl, $C_1$-$C_{15}$ alkoxy, amino, mono($C_1$-$C_{15}$)alkylamino, di($C_1$-$C_{15}$)alkylamino, ($C_1$-$C_{15}$)alkyl-carbonyl, amido, ($C_1$-$C_{15}$)alkoxycarbonyl, mono($C_1$-$C_{15}$)alkylaminocarbonyl and di($C_1$-$C_{15}$) alkylaminocarbonyl groups;

$R_1$ is chosen from a hydrogen atom, a $C_1$-$C_{15}$ alkyl radical, a $C_1$-$C_{15}$ alkoxy radical, a (($C_1$-$C_{15}$)alkoxy)$C_1$-$C_{15}$alkyl radical, a $C_1$-$C_{15}$ hydroxyalkoxy radical, a $C_1$-$C_{15}$ monohydroxyalkyl radical, a $C_1$-$C_{15}$ polyhydroxyalkyl radical, and a halogen atom;

n is an integer ranging from 1 to 4;

with the exception of the following compounds:

N-(3-isopropoxypropyl)benzene-1,4-diamine; and

N-(1-methylpropoxypropyl)benzene-1,4-diamine.

2. The compound of claim 1, wherein group R of formula (I) is chosen from: a linear (linear ($C_1$-$C_5$)alkoxy)($C_5$-$C_8$) alkyl radical; a branched (linear ($C_1$-$C_5$)alkoxy)($C_3$-$C_7$)alkyl radical; a (branched ($C_3$-$C_7$)alkoxy)($C_2$-$C_6$)alkyl radical; and a linear or branched (($C_1$-$C_6$)alkoxy)($C_2$-$C_6$)alkyl radical substituted with at least one group chosen from hydroxyl, $C_1$-$C_5$ alkoxy, amino, mono($C_1$-$C_5$)alkylamino, di($C_1$-$C_5$)

alkylamino, $(C_1-C_5)$alkylcarbonyl, amido, $(C_1-C_5)$alkoxycarbonyl, mono$(C_1-C_5)$alkylaminocarbonyl and di$(C_1-C_5)$alkylaminocarbonyl groups.

3. The compound of claim 1, wherein group $R_1$ of formula (I) is chosen from: a hydrogen atom, a $C_1-C_5$ alkyl radical, a $C_1-C_5$ alkoxy radical, a $((C_1-C_5)$alkoxy$)(C_1-C_5)$alkyl radical, a $C_1-C_5$ hydroxyalkoxy radical, a $C_1-C_5$ monohydroxyalkyl radical, a $C_1-C_5$ polyhydroxyalkyl radical, a chlorine atom, and a bromine atom.

4. A compound, wherein the compound is chosen from the following compounds:
— N-(2-Methoxy-1-methylethyl)benzene-1,4-diamine;
— N-(1-Methoxymethylpropyl)benzene-1,4-diamine;
N-[3-(2-Ethylhexyloxy)propyl]benzene-1,4-diamine;
-1-(4-Aminophenylamino)-3-methoxypropan-2-ol;
— N-(4-Methoxybutyl) benzene-1,4-diamine;
— N-(5-Methoxypentyl)benzene-1,4-diamine;
— N-(6-Methoxyhexyl)benzene-1,4-diamine;
— N-(6-Ethoxyhexyl)benzene-1,4-diamine;
— N-(6-Isopropoxyhexyl)benzene-1,4-diamine;
— N-(2-Isopropoxyethyl)benzene-1,4-diamine;
— N-(2-tert-Butoxyethyl)benzene-1,4-diamine;
— N-1-(2-Methoxy-1-methylethyl)-2-methylbenzene-1,4-diamine;
— N-1-(1-Methoxymethylpropyl)-2-methylbenzene-1,4-diamine;
— N-1-(3-Isopropoxypropyl)-2-methylbenzene-1,4-diamine;
— N-1-[3-(2-Ethylhexyloxy)propyl]-2-methylbenzene-1,4-diamine;
-1-(4-Amino-2-methylphenylamino)-3-methoxypropan-2-ol;
— N-1-(4-Methoxybutyl)-2-methylbenzene-1,4-diamine;
— N-1-(5-Methoxypentyl)-2-methylbenzene-1,4-diamine;
— N-1-(6-Methoxyhexyl)-2-methylbenzene-1,4-diamine;
— N-1-(6-Ethoxyhexyl)-2-methylbenzene-1,4-diamine;
— N-1-(6-Isopropoxyhexyl)-2-methylbenzene-1,4-diamine;
— N-1-(2-Isopropoxyethyl)-2-methylbenzene-1,4-diamine;
— N-1-(2-tert-Butoxyethyl)-2-methylbenzene-1,4-diamine;
— N-4-(2-Methoxy-1-methylethyl)-2-methylbenzene-1,4-diamine;
— N-4-(1-Methoxymethylpropyl)-2-methylbenzene-1,4-diamine;
— N-4-(3-Isopropoxypropyl)-2-methylbenzene-1,4-diamine;
— N-4-[3-(2-Ethylhexyloxy)propyl]-2-methylbenzene-1,4-diamine;
-1-(4-Amino-3-methylphenylamino)-3-methoxypropan-2-ol;
— N-4-(4-Methoxybutyl)-2-methylbenzene-1,4-diamine;
— N-4-(5-Methoxypentyl)-2-methylbenzene-1,4-diamine;
— N-4-(6-Methoxyhexyl)-2-methylbenzene-1,4-diamine;
— N-4-(6-Ethoxyhexyl)-2-methylbenzene-1,4-diamine;
— N-4-(6-Isopropoxyhexyl)-2-methylbenzene-1,4-diamine;
— N-4-(2-Isopropoxyethyl)-2-methylbenzene-1,4-diamine;
— N-4-(2-tert-Butoxyethyl)-2-methylbenzene-1,4-diamine;
and the addition salts thereof.

5. The compound of claim 1, wherein the addition-salts of formula (I) are chosen from the hydrochlorides, hydrobromides, sulfates, citrates, succinates, tartrates, lactates, tosylates, benzenesulfonates, phosphates and acetates thereof.

6. A nitro compound, wherein the nitro compound has the structure (II) below:

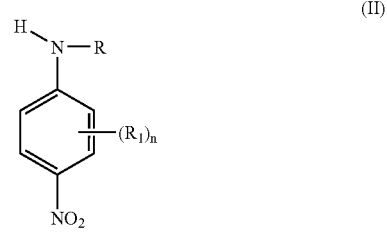

in which:
R is chosen from a linear (linear $(C_1-C_{10})$alkoxy$)(C_5-C_{10})$ alkyl radical, a branched (linear $(C_1-C_{10})$alkoxy$)(C_3-C_{10})$alkyl radical, a (branched $(C_3-C_{10})$alkoxy$)(C_2-C_{10})$ alkyl radical, and a linear or branched $((C_1-C_{10})$alkoxy$)$ $(C_2-C_{10})$alkyl radical substituted with at least one group chosen from hydroxyl, $C_1-C_{15}$ alkoxy, amino, mono$(C_1-C_{15})$alkylamino, $(C_1-C_{15})$alkylcarbonyl, amido, $(C_1-C_{15})$alkoxycarbonyl, mono$(C_1-C_{15})$alkylaminocarbonyl and di$(C_1-C_{15})$alkylaminocarbonyl groups;

$R_1$ is chosen from a hydrogen atom, a $C_1-C_{15}$ alkyl radical, a $C_1-C_{15}$ alkoxy radical, a $((C_1-C_{15})$alkoxy$)C_1-C_{15}$alkyl radical, a $C_1-C_{15}$ hydroxyalkoxy radical, a $C_1-C_{15}$ monohydroxyalkyl radical, a $C_1-C_{15}$ polyhydroxyalkyl radical, and a halogen atom, and;

n is an integer ranging from 1 to 4.

7. A process for preparing a compound of formula (I) below:

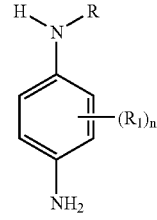

comprising reducing a nitro compound of formula (II) below:

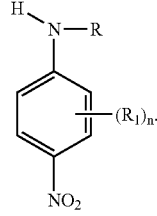

wherein in both of said formula (I) and (II):
R is chosen from a linear (linear $(C_1-C_{10})$alkoxy$)(C_5-C_{10})$ alkyl radical, a branched (linear $(C_1-C_{10})$alkoxy$)(C_3-C_{10})$alkyl radical, a (branched $(C_3-C_{10})$alkoxy$)(C_2-C_{10})$ alkyl radical, and a linear or branched $((C_1-C_{10})$alkoxy$)$ $(C_2-C_{10})$alkyl radical substituted with at least one group chosen from hydroxyl, $C_1-C_{15}$ alkoxy, amino, mono$(C_1-C_{15})$alkylamino, $(C_1-C_{15})$alkylcarbonyl, amido, $(C_1-C_{15})$alkoxycarbonyl, mono$(C_1-C_{15})$alkylaminocarbonyl and di$(C_1-C_{15})$alkylaminocarbonyl groups;

$R_1$ is chosen from a hydrogen atom, a $C_1-C_{15}$ alkyl radical, a $C_1-C_{15}$ alkoxy radical, a $((C_1-C_{15})$alkoxy$)C_1-C_{15}$alkyl radical, a $C_1$-$C_{15}$ hydroxyalkoxy radical, a $C_1$-$C_{15}$ monohydroxyalkyl radical, a $C_1$-$C_{15}$ polyhydroxyalkyl radical, and a halogen atom, and;

n is an integer ranging from 1 to 4, with the proviso that the following compounds are excluded from the compounds of formula (I):

N-(3-isopropoxypropyl)benzene-1,4-diamine; and

N-(1-methylpropoxypropyl)benzene-1,4-diamine.

8. A cosmetic composition for dyeing keratin fibers, comprising, in a medium that is suitable for dyeing, at least one compound chosen from secondary para-phenylenediamines of formula (I) and the addition salts thereof:

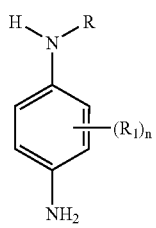

wherein:

R is chosen from a linear (linear ($C_1$-$C_{10}$)alkoxy)($C_5$-$C_{10}$) alkyl radical, a branched (linear ($C_1$-$C_{10}$)alkoxy)($C_3$-$C_{10}$)alkyl radical, a (branched ($C_3$-$C_{10}$)alkoxy)($C_2$-$C_{10}$) alkyl radical, and a linear or branched (($C_1$-$C_{10}$)alkoxy) ($C_2$-$C_{10}$)alkyl radical substituted with at least one group chosen from hydroxyl, $C_1$-$C_{15}$ alkoxy, amino, mono($C_1$-$C_{15}$)alkylamino, di($C_1$-$C_{15}$)alkylamino, ($C_1$-$C_{15}$)alkylcarbonyl, amido, ($C_1$-$C_{15}$)alkoxycarbonyl, mono($C_1$-$C_{15}$)alkylaminocarbonyl and di($C_1$-$C_{15}$) alkylaminocarbonyl groups;

$R_1$ is chosen from a hydrogen atom, a $C_1$-$C_{15}$ alkyl radical, a $C_1$-$C_{15}$ alkoxy radical, a (($C_1$-$C_{15}$)alkoxy)$C_1$-$C_{15}$alkyl radical, a $C_1$-$C_{15}$ hydroxyalkoxy radical, a $C_1$-$C_{15}$ monohydroxyalkyl radical, a $C_1$-$C_{15}$ polyhydroxyalkyl radical, and a halogen atom; and n is an integer ranging from 1 to 4.

9. A cosmetic composition for dyeing keratin fibers, comprising, in a medium suitable for dyeing, at least one compound chose from:

—N-(2-Methoxy-1-methylethyl)benzene-1,4-diamine;
—N-(1-Methoxymethylpropyl)benzene-1,4-diamine;
—N-(3-Isopropoxypropyl)benzene-1,4-diamine;
—N-[3-(2-Ethylhexyloxy)propyl]benzene-1,4-diamine;
-1-(4-Aminophenylamino)-3-methoxypropan-2-ol;
—N-(4-Methoxybutyl)benzene-1,4-diamine;
—N-(5-Methoxypentyl)benzene-1,4-diamine;
—N-(6-Methoxyhexyl)benzene-1,4-diamine;
—N-(6-Ethoxyhexyl)benzene-1,4-diamine;
—N-(6-Isopropoxyhexyl)benzene-1,4-diamine;
—N-(2-Isopropoxyethyl)benzene-1,4-diamine;
—N-(2-tert-Butoxyethyl)benzene-1,4-diamine;
—N-1-(2-Methoxy-1-methylethyl)-2-methylbenzene-1,4-diamine;
—N-1-(1-Methoxymethylpropyl)-2-methylbenzene-1,4-diamine;
—N-1-(3-Isopropoxypropyl)-2-methylbenzene-1,4-diamine;
—N-1-[3-(2-Ethylhexyloxy)propyl]-2-methylbenzene-1,4-diamine;
-1-(4-Amino-2-methylphenylamino)-3-methoxypropan-2-ol;
—N-1-(4-Methoxybutyl)-2-methylbenzene-1,4-diamine;
—N-1-(5-Methoxypentyl)-2-methylbenzene-1,4-diamine;
—N-1-(6-Methoxyhexyl)-2-methylbenzene-1,4-diamine;
—N-1-(6-Ethoxyhexyl)-2-methylbenzene-1,4-diamine;
—N-1-(6-Isopropoxyhexyl)-2-methylbenzene-1,4-diamine;
—N-1-(2-Isopropoxyethyl)-2-methylbenzene-1,4-diamine;
—N-1-(2-tert-Butoxyethyl)-2-methylbenzene-1,4-diamine;
—N-4-(2-Methoxy-1-methylethyl)-2-methylbenzene-1,4-diamine;
—N-4-(1-Methoxymethylpropyl)-2-methylbenzene-1,4-diamine;
—N-4-(3-Isopropoxypropyl)-2-methylbenzene-1,4-diamine;
—N-4-[3-(2-Ethylhexyloxy)propyl]-2-methylbenzene-1,4-diamine;
-1-(4-Amino-3-methylphenylamino)-3-methoxypropan-2-ol;
—N-4-(4-Methoxybutyl)-2-methylbenzene-1,4-diamine;
—N-4-(5-Methoxypentyl)-2-methylbenzene-1,4-diamine;
—N-4-(6-Methoxyhexyl)-2-methylbenzene-1,4-diamine;
—N-4-(6-Ethoxyhexyl)-2-methylbenzene-1,4-diamine;
—N-4-(6-Isopropoxyhexyl)-2-methylbenzene-1,4-diamine;
—N-4-(2-Isopropoxyethyl)-2-methylbenzene-1,4-diamine;
—N-4-(2-tert-Butoxyethyl)-2-methylbenzene-1,4-diamine;

and the addition salts thereof.

10. The cosmetic composition of claim 8, wherein the compound of formula (I) is present in an amount ranging from 0.0001% to 20% by weight relative to the total weight of the composition.

11. The cosmetic composition of claim 10, wherein the compound of formula (I) is present in an amount ranging from 0.005% to 6% by weight relative to the total weight of the composition.

12. The cosmetic composition of claim 8, wherein the medium that is suitable for dyeing consists of water or comprises a mixture of water and at least one organic solvent chosen from branched or unbranched $C_1$-$C_4$ lower alcohols; polyols; polyol ethers; aromatic alcohols; and mixtures thereof.

13. The cosmetic composition of claim 8, further comprising at least one cosmetic adjuvant chosen from antioxidants; penetrating agents; sequestering agents; fragrances; buffers; dispersants; surfactants; conditioning agents; film-forming agents; polymers; ceramides; preserving agents; nacreous agents; opacifiers; and vitamins or provitamins.

14. The cosmetic composition of claim 13, wherein the amount of each cosmetic adjuvant contained in the composition ranges from 0.01% to 20% by weight relative to the total weight of the composition.

15. The cosmetic composition of claim 8, wherein the composition further comprises at least one oxidation coupler chosen from meta-phenylenediamines; meta-aminophenols; meta-diphenols; naphthalene-based couplers; heterocyclic couplers; and the addition salts thereof.

16. The cosmetic composition of claim 15, wherein the at least one coupler is present in an amount ranging from 0.0001% to 20% by weight relative to the total weight of the composition.

17. The cosmetic composition of claim 8, wherein the composition further comprises at least one additional oxidation base other than the compound of formula (I), chosen from para-phenylenediamines, bis(phenyl)alkylenediamines, para-aminophenols, ortho-aminophenols and heterocyclic bases, and the addition salts thereof.

18. The cosmetic composition of claim 17, wherein the at least one additional oxidation base is present in an amount ranging from 0.0001% to 20% by weight relative to the total weight of the composition.

19. The cosmetic composition of claim 8, further comprising at least one natural or cationic direct dye.

20. A process for dyeing keratin fibers, comprising applying to keratin fibers, in the presence of an oxidizing agent and for a time sufficient to develop a desired coloration, a cosmetic composition, comprising, in a medium suitable for dyeing, at least one secondary para-phenylenediamine chosen from compounds of formula (I) and the addition salts thereof:

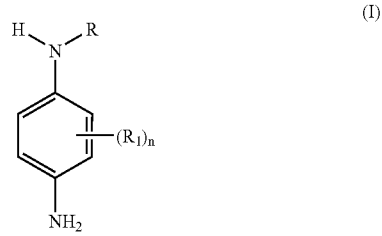

(I)

wherein:

R is chosen from: a linear (linear $(C_1-C_{10})$alkoxy)$(C_5-C_{10})$ alkyl radical; a branched (linear $(C_1-C_{10})$alkoxy)$(C_3-C_{10})$alkyl radical; a (branched $(C_3-C_{10})$alkoxy)$(C_2-C_{10})$ alkyl radical; and a linear or branched $((C_1-C_{10})$alkoxy)$(C_2-C_{10})$alkyl radical substituted with at least one group chosen from hydroxyl, $C_1-C_{15}$ alkoxy, amino, mono$(C_1-C_{15})$alkylamino, di$(C_1-C_{15})$alkylamino, $(C_1-C_{15})$alkylcarbonyl, amido, $(C_1-C_{15})$alkoxycarbonyl, mono$(C_1-C_{15})$alkylaminocarbonyl and di$(C_1-C_{15})$alkylaminocarbonyl groups;

$R_1$ is chosen from a hydrogen atom, a $C_1-C_{15}$ alkyl radical, a $C_1-C_{15}$ alkoxy radical, a $((C_1-C_{15})$alkoxy)$C_1-C_{15}$alkyl radical, a $C_1-C_{15}$ hydroxyalkoxy radical, a $C_1-C_{15}$ monohydroxyalkyl radical, a $C_1-C_{15}$ polyhydroxyalkyl radical, and a halogen atom; and n is an integer ranging from 1 to 4.

21. A ready-to-use composition, comprising:

a dye composition comprising at least one secondary para-phenylenediamine compound chosen from the compounds of formula (I):

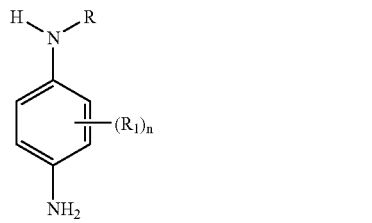

wherein:

R is chosen from: a linear (linear $(C_1-C_{10})$alkoxy)$(C_5-C_{10})$ alkyl radical; a branched (linear $(C_1-C_{10})$alkoxy)$(C_3-C_{10})$alkyl radical; a (branched $(C_3-C_{10})$alkoxy)$(C_2-C_{10})$ alkyl radical; and a linear or branched $((C_1-C_{10})$alkoxy)$(C_2-C_{10})$alkyl radical substituted with at least one group chosen from hydroxyl, $C_1-C_{15}$ alkoxy, amino, mono$(C_1-C_{15})$alkylamino, di$(C_1-C_{15})$alkylamino, $(C_1-C_{15})$alkylcarbonyl, amido, $(C_1-C_{15})$alkoxycarbonyl, mono$(C_1-C_{15})$alkylaminocarbonyl and di$(C_1-C_{15})$alkylaminocarbonyl groups;

$R_1$ is chosen from a hydrogen atom, a $C_1-C_{15}$ alkyl radical, a $C_1-C_{15}$ alkoxy radical, a $((C_1-C_{15})$alkoxy)$C_1-C_{15}$alkyl radical, a $C_1-C_{15}$ hydroxyalkoxy radical, a $C_1-C_{15}$ monohydroxyalkyl radical, a $C_1-C_{15}$ polyhydroxyalkyl radical, and a halogen atom; and n is an integer ranging from 1 to 4, and at least one oxidizing agent chosen from hydrogen peroxide, urea peroxide, alkali metal bromates, persalts, peracids and oxidase enzymes.

22. A multi-compartment kit comprising at least one first compartment comprising an oxidation dye composition, comprising, in a medium suitable for dyeing keratin fibers, at least one compound chosen from those of formula (I) and the addition salts thereof:

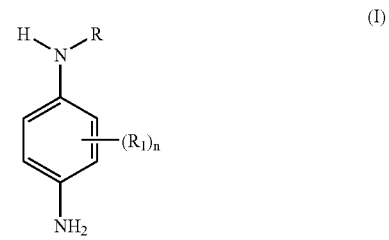

(I)

wherein:

R is chosen from: a linear (linear $(C_1-C_{10})$alkoxy)$(C_5-C_{10})$ alkyl radical; a branched (linear $(C_1-C_{10})$alkoxy)$(C_3-C_{10})$alkyl radical; a (branched $(C_3-C_{10})$alkoxy)$(C_2-C_{10})$ alkyl radical; and a linear or branched $((C_1-C_{10})$alkoxy)$(C_2-C_{10})$alkyl radical substituted with at least one group chosen from hydroxyl, $C_1-C_{15}$ alkoxy, amino, mono$(C_1-C_{15})$alkylamino, di$(C_1-C_{15})$alkylamino, $(C_1-C_{15})$alkylcarbonyl, amido, $(C_1-C_{15})$alkoxy-carbonyl, mono$(C_1-C_{15})$alkylaminocarbonyl and di$(C_1-C_{15})$alkylaminocarbonyl groups;

$R_1$ is chosen from a hydrogen atom, a $C_1-C_{15}$ alkyl radical, a $C_1-C_{15}$ alkoxy radical, a $((C_1-C_{15})$alkoxy)$C_1-C_{15}$ alkyl radical, a $C_1-C_{15}$ hydroxyalkoxy radical, a $C_1-C_{15}$ monohydroxyalkyl radical, a $C_1-C_{15}$ polyhydroxyalkyl radical, and a halogen atom; and n is an integer ranging from 1 to 4, and at least one second compartment comprising at least one oxidizing agent.

* * * * *

UNITED STATES PATENT AND TRADEMARK OFFICE
CERTIFICATE OF CORRECTION

| | | |
|---|---|---|
| PATENT NO. | : 7,435,267 B2 | Page 1 of 1 |
| APPLICATION NO. | : 11/066449 | |
| DATED | : October 14, 2008 | |
| INVENTOR(S) | : Stéphane Sabelle et al. | |

It is certified that error appears in the above-identified patent and that said Letters Patent is hereby corrected as shown below:

In claim 5, column 43, line 66, "addition-salts" should read --addition salts--.

In claim 7, column 44, line 51, the structure should be:

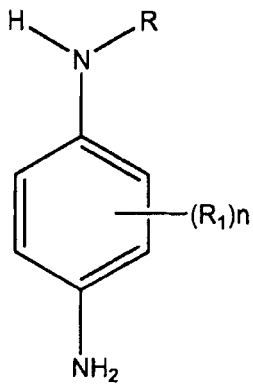

with no "." next to the variable n.

In claim 7, column 44, line 56, "and (II):" should read --and formula (II):--.

In claim 9, column 45, line 44, "chose" should read --chosen--.

In claim 22, column 48, line 50, "$(C_1-C_{15})$alkoxy-carbonyl," should read --$(C_1-C_{15})$alkoxycarbonyl,--.

Signed and Sealed this

Third Day of March, 2009

JOHN DOLL
*Acting Director of the United States Patent and Trademark Office*